US008739804B2

(12) United States Patent
Cohen et al.

(10) Patent No.: US 8,739,804 B2
(45) Date of Patent: Jun. 3, 2014

(54) REMOVAL MECHANISM FOR ADHESIVE EYE STRIPS

(75) Inventors: Daniel E. Cohen, Eden Prairie, MN (US); Steven Thomas Winkler, Walnut Creek, CA (US)

(73) Assignee: Victoria McGill Enterprises, Inc., San Francisco, CA (US)

( * ) Notice: Subject to any disclaimer, the term of this patent is extended or adjusted under 35 U.S.C. 154(b) by 0 days.

(21) Appl. No.: 13/497,742

(22) PCT Filed: Sep. 22, 2010

(86) PCT No.: PCT/US2010/049755
§ 371 (c)(1), (2), (4) Date: Mar. 22, 2012

(87) PCT Pub. No.: WO2011/037956
PCT Pub. Date: Mar. 31, 2011

(65) Prior Publication Data

US 2012/0239079 A1 Sep. 20, 2012

Related U.S. Application Data

(60) Provisional application No. 61/244,673, filed on Sep. 22, 2009.

(51) Int. Cl.

| | |
|---|---|
| ***A45D 40/30*** | (2006.01) |
| ***A45D 24/00*** | (2006.01) |
| ***A45D 40/26*** | (2006.01) |
| ***A61F 5/08*** | (2006.01) |
| ***B32B 9/00*** | (2006.01) |
| ***B32B 33/00*** | (2006.01) |
| ***B65D 73/00*** | (2006.01) |
| ***A61F 13/00*** | (2006.01) |
| ***A61F 15/00*** | (2006.01) |
| ***G09F 3/10*** | (2006.01) |
| ***A45D 44/12*** | (2006.01) |
| ***A45D 44/22*** | (2006.01) |

(52) U.S. Cl.
CPC ................ *A45D 40/30* (2013.01); *A45D 44/12* (2013.01); *A45D 44/22* (2013.01); *G09F 3/10* (2013.01)
USPC ........................................................ 132/200

(58) Field of Classification Search
CPC ..... A45D 40/30; A45D 44/002; A45D 44/12; A45D 44/22; A41G 5/02; A61F 13/124; A61F 13/0236; A61F 2013/00812; B65D 71/0085; G09F 3/02; G09F 3/10
USPC ........... 132/200, 201, 333, 212, 213, 216, 73, 132/319, 320, 286, 218; 606/204.25, 606/204.35; 128/858, 857; 206/575, 440, 206/460, 484, 813, 824, 565; 229/924–926; D9/727; 434/377; 428/42.1, 40.1, 42.2, 428/41.8, 43; 600/236; 602/54, 74, 57, 79; 40/594, 638
See application file for complete search history.

(56) References Cited

U.S. PATENT DOCUMENTS 2,001,862 A * 5/1935 Carter ...................... 606/204.35
2,239,040 A * 4/1941 Holmes ........................ 132/285

(Continued)

*Primary Examiner* — Vanitha Elgart

(74) *Attorney, Agent, or Firm* — Briggs and Morgan, P.A.; Aleya R. Champlin; Audrey J. Babcock

(57) ABSTRACT

A mechanism for releasing an eye strip from a backing material card is described. The backing material card includes a movable flap that releases a right and/or left undamaged end of a strip (for right or left hand preference) into free space in order to conveniently lift the strip off the backing material, preferably between the user's thumb and index finger, for proper orientation and placement on the eyelid.

15 Claims, 6 Drawing Sheets

(56) References Cited

U.S. PATENT DOCUMENTS

| | | | | | |
|---|---|---|---|---|---|
| 2,288,386 | A | * | 6/1942 | Belden | 132/73 |
| 2,563,689 | A | * | 8/1951 | Muhlhauser | 128/846 |
| 2,835,259 | A | * | 5/1958 | Goodman | 132/53 |
| 3,068,863 | A | * | 12/1962 | Bowman | 128/858 |
| 3,315,387 | A | * | 4/1967 | Heuser | 40/638 |
| 3,440,746 | A | * | 4/1969 | Richards | 40/595 |
| 3,485,251 | A | * | 12/1969 | Brunet | 132/216 |
| 3,935,872 | A | * | 2/1976 | Aylott | 132/216 |
| 3,944,692 | A | * | 3/1976 | Swenson | 428/41.8 |
| 4,015,352 | A | * | 4/1977 | Prange | 40/594 |
| 4,018,336 | A | * | 4/1977 | Aylott | 206/460 |
| 4,024,879 | A | * | 5/1977 | Stryker | 132/216 |
| 4,055,249 | A | * | 10/1977 | Kojima | 206/447 |
| 4,587,146 | A | * | 5/1986 | Anhauser et al. | 428/42.2 |
| 4,653,483 | A | | 3/1987 | Clavin | |
| 4,747,782 | A | * | 5/1988 | Campbell, Jr. | 434/377 |
| 4,787,158 | A | * | 11/1988 | Vitol | 40/638 |
| 4,944,040 | A | * | 7/1990 | Riedel et al. | 2/15 |
| 4,947,876 | A | * | 8/1990 | Larsen | 132/73 |
| 5,242,381 | A | * | 9/1993 | Hoffmann et al. | 602/57 |
| 5,384,174 | A | * | 1/1995 | Ward et al. | 428/41.5 |
| 5,525,389 | A | * | 6/1996 | Hoffmann et al. | 428/41.5 |
| 5,643,188 | A | * | 7/1997 | Oliveira | 602/54 |
| 5,788,284 | A | * | 8/1998 | Hirst | 283/81 |
| 5,860,433 | A | * | 1/1999 | Halpern | 132/319 |
| 5,887,590 | A | * | 3/1999 | Price | 128/858 |
| 6,161,554 | A | * | 12/2000 | Dunlap-Harris | 132/216 |
| 6,190,346 | B1 | | 2/2001 | McGill | |
| 6,193,741 | B1 | | 2/2001 | Heavenridge et al. | |
| 6,277,458 | B1 | * | 8/2001 | Dirksing et al. | 428/42.3 |
| 6,336,462 | B1 | * | 1/2002 | Santelli et al. | 132/319 |
| 6,733,856 | B2 | * | 5/2004 | Nojiri | 428/40.1 |
| 6,977,106 | B2 | * | 12/2005 | Billings | 428/40.1 |
| 7,625,619 | B2 | * | 12/2009 | Hodson et al. | 428/40.1 |
| 8,051,860 | B1 | * | 11/2011 | Pereira | 132/200 |
| 8,074,667 | B2 | * | 12/2011 | Villanueva | 132/319 |
| 2003/0234028 | A1 | * | 12/2003 | Edell | 132/319 |
| 2004/0074502 | A1 | * | 4/2004 | Abbasi | 128/858 |
| 2004/0138699 | A1 | * | 7/2004 | Lish | 606/204.35 |
| 2005/0089663 | A1 | * | 4/2005 | Wong et al. | 428/42.3 |
| 2005/0159775 | A1 | | 7/2005 | Reynolds | |
| 2006/0272671 | A1 | * | 12/2006 | Dobler et al. | 132/320 |
| 2007/0107745 | A1 | * | 5/2007 | Kiyomoto | 132/73 |
| 2007/0212509 | A1 | * | 9/2007 | Herbig et al. | 428/40.1 |
| 2009/0075010 | A1 | * | 3/2009 | Flynn | 428/42.3 |
| 2009/0234382 | A1 | * | 9/2009 | Dillon | 606/204.35 |
| 2013/0089584 | A1 | * | 4/2013 | Jager Lezer et al. | 424/401 |

* cited by examiner

REMOVAL MECHANISM FOR ADHESIVE EYE STRIPS

BACKGROUND

To achieve a more youthful eyelid appearance, an adhesive eye strip can be placed on the upper eyelid of a user to tuck and hold droopy upper eyelid skin in its youthful position. One side of the strip is convex and is placed toward the back of the upper eyelid in order to recreate the person's natural eyelid crease, causing the eyelid skin to assume a more youthful position and not droop toward or over the border of the upper lid. More details about adhesive eye strips as referred to in the present application can be found in U.S. Pat. Nos. 6,190,346 and 6,193,741, the entire contents of which are incorporated by reference herein. One example of an adhesive eye strip includes a small adhesive strip with one straight edge and one convex edge, the strip having an overall midline length of approximately 25 mm, and a width of about 5 mm wide at its midpoint, and a width of about 1.7 mm at each of its rounded ends. Any type of adhesive eye strip may be used with the removal mechanism of the present invention.

The adhesive eye strip can achieve its desired function only if it can be placed properly on the eyelid by the user. The most difficult challenge in doing so is removing the small, thin, adhesive coated strip from its backing material, first without damaging it and second, in a manner that enables lifting the strip off the backing material with the proper orientation for application. In order to have the greatest ease in orienting the strip properly on the eyelid it is preferable to be able to pick one end of it off the backing material between the user's thumb and index finger of their left or right hand, whichever is preferred.

Each eye strip consists of a thin and flexible or very flexible material coated with an adhesive layer (in one example, the total strip thickness is approximately 0.004 inches) and adhered to a backing material having a release coating. Due to the thinness of the strip material and adhesive coating and the small size of each end, it is difficult to remove it from its backing material without damaging it. Often, strip removal from the backing material using one's fingernail to pry up one end of the strip causes it to fold under and adhere to itself (adhesive to adhesive) rendering the strip useless or causing an upward curling of the end making placement more difficult and making it less likely to adhere to the skin.

SUMMARY OF THE INVENTION

A mechanism that exposes an end of an eye strip into free space is described in order to conveniently lift the strip off the backing material, preferably between the user's thumb and index finger, for proper orientation and placement on the eyelid. The mechanism includes providing a backing material card having a continuous cut to create a movable flap on the card from which the eye strip can be removed. A method for using the mechanism is also described.

DETAILED DESCRIPTION

Figure 1:
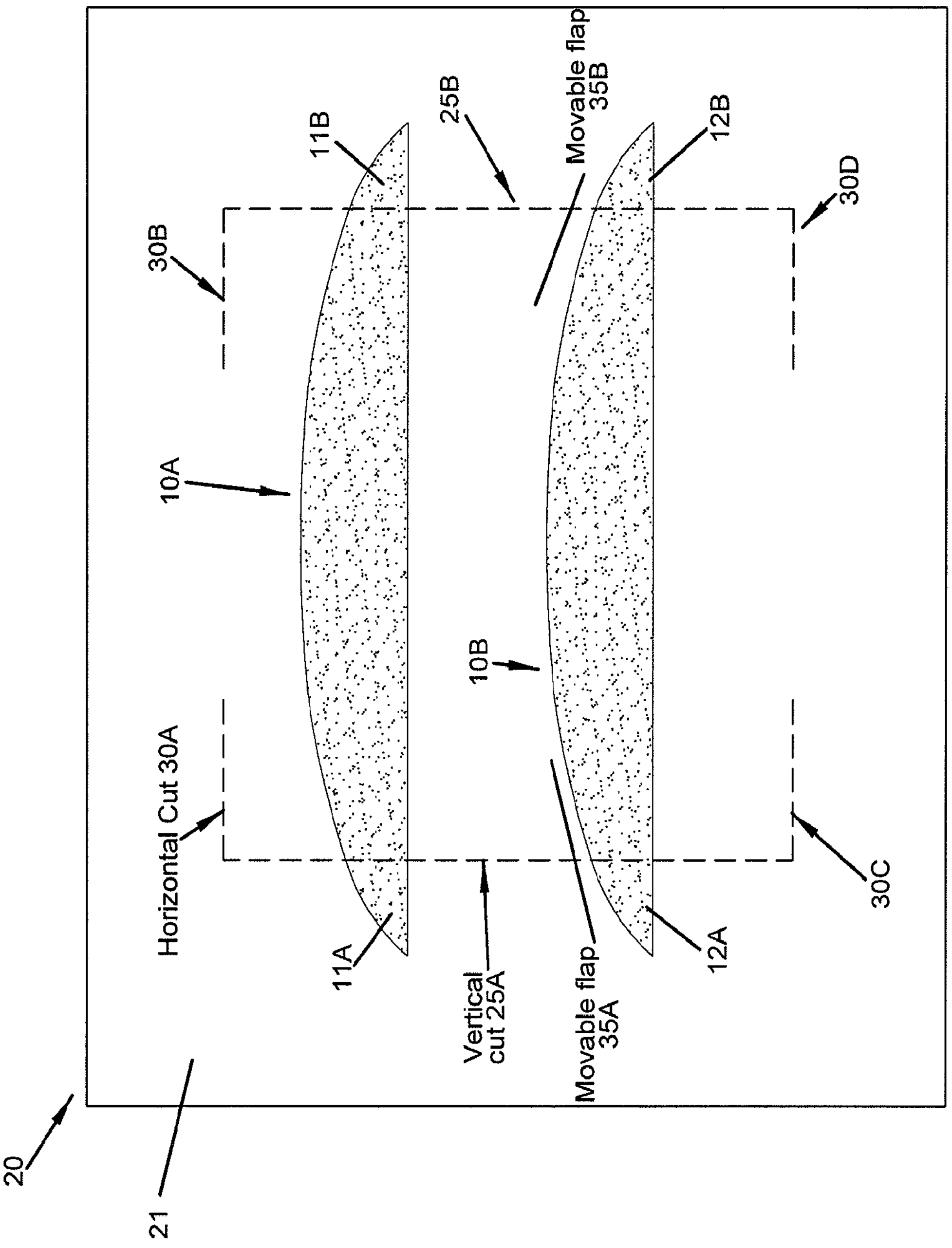
FIG. 1 is a diagram showing one embodiment including two eye strips 10A and 10B positioned on the backing material card 20.

FIG. 1 shows strips 10A and 10B (oriented horizontally on backing material card 20 on its front surface 21) which straddle vertical cuts 25A and 25B (each approximately 15 mm long) in the backing material 20 approximately 3 mm proximal to each end region 11A and 11B of the strip 10A, and each end region 12A and 12B of strip 10B. A horizontal cut, shown as 30A-D in FIG. 1 (approximately 7 mm long) from each end of the vertical cut extends toward the center of the strip creating a movable flap 35A and 35B of backing material at both ends of each pair of strips.

As shown in the figures, the horizontal and vertical or curved cuts in the backing material should preferably be actual continuous cuts through the entire thickness of the backing material, and not perforations. The dashed lines in the figures showing the front surface of the backing material reflect the fact that the cuts are present behind the adhesive eye strips. The figures showing the back surface of the backing material show the continuity of the cuts in the backing material.

To remove a strip from the backing card, the card 20 with front surface 21 facing the user (strip side up) should be oriented so that the curved side of the strip faces toward the user or downward because the curved side of the strip is to be placed toward the back of the eyelid. Then the user should hold the edge or middle of the backing material card 20, adjacent to a pair of strips 10A and 10B, between thumb (front surface 21 or strip side of card) and index finger (back surface 22 or underside of card) of his or her hand, depending on whether he or she wants to pick up the left or right side of the strip with either his or her left or right hand.

Figure 2:
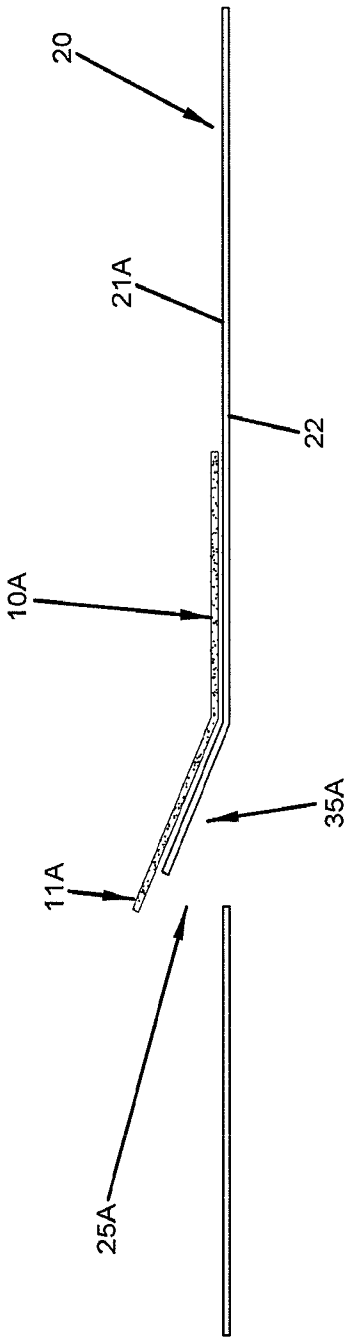
FIG. 2 is a side view of one end of an eye strip 10A being lifted off of the backing material card 20.

While holding the backing material card with front surface 21 facing the user (strip side up), the user should press upward on back surface 22 from under the strip with their other index finger just medial to the vertical cut and between both horizontal cut extensions under the end of interest, forcing the flap 35A or 35B of backing material card 20 to move upward so that the end region 11A or 11B, and end region 12A or 12B, lateral to the vertical cut, lift off the backing material and extend into free space without folding or curling, as shown in FIG. 2. FIG. 2 shows a side or edge view of backing material card 20 with flap 35A pushed up, revealing an end region 11A of strip 10A, making it very easy for the user to lift strip 10A up and off the front surface 21 of backing material card 20 without damaging, folding or curling strip 10A.

Figure 4A:
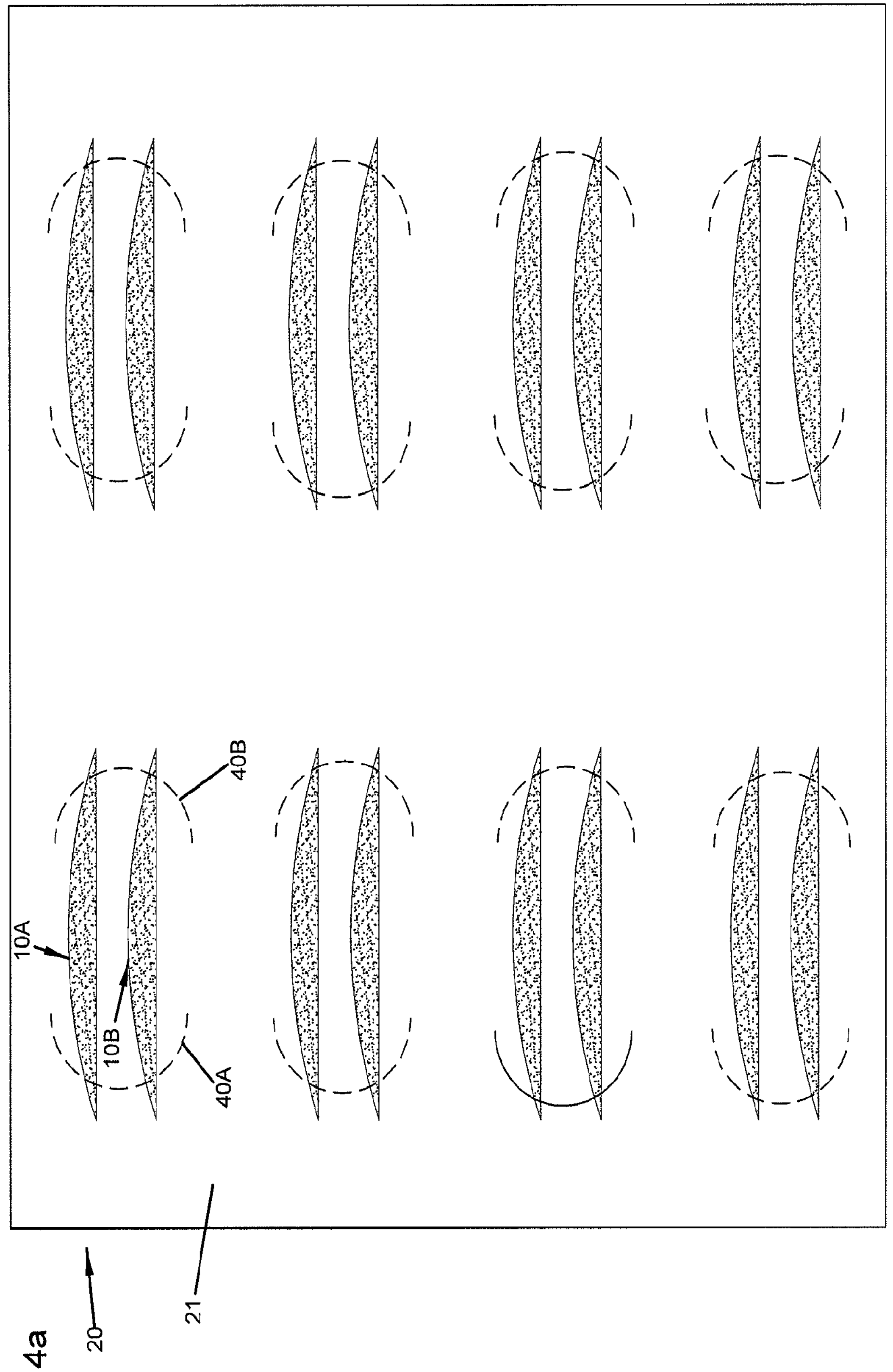
FIG. 4*a* is a diagram showing a different embodiment of the invention including eight pairs of eye strips 10A and 10B positioned on the backing material card 20.
Figure 4B:
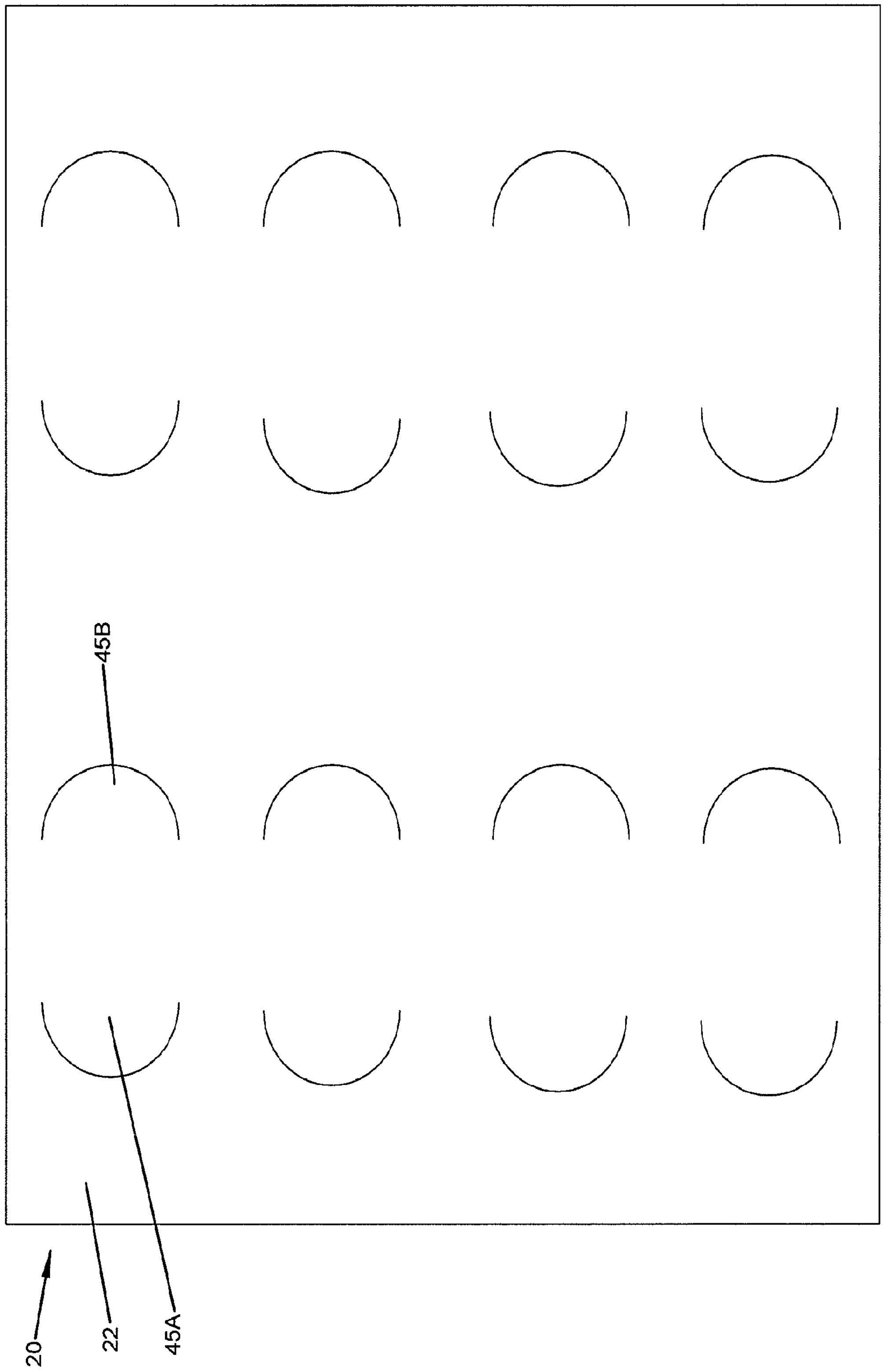
FIG. 4*b* is a diagram showing the back 24 of the embodiment shown in FIG. 4*a*.

Another embodiment of the invention includes the use of curved or rounded cuts rather than vertical and horizontal cuts, as shown in FIGS. 4*a* and 4*b*. Similar to the embodiment described above, the user presses upward on back surface 22 from behind the backing material card 20 under the desired (left or right) cut 40A or 40B to lift flap 45A or 45B upward from front surface 21 of card 20, so that the end region 11A or 11B, and end region 12A or 12B, lateral to the curved cut 40A or 40B, lift off of the backing material and into free space without folding or curling, similar to the embodiment shown in FIG. 2.

To cause the ends of the strip to lift off the backing material, without undue effort or force, the upward force required to be placed on the backing material card should not be in excess of 500 grams, as measured by applying pressure with a 0.3 inch diameter circular probe (approximating the size of part of one's index finger tip that could be applied to the underside of the cut backing material card).

Figure 3A:
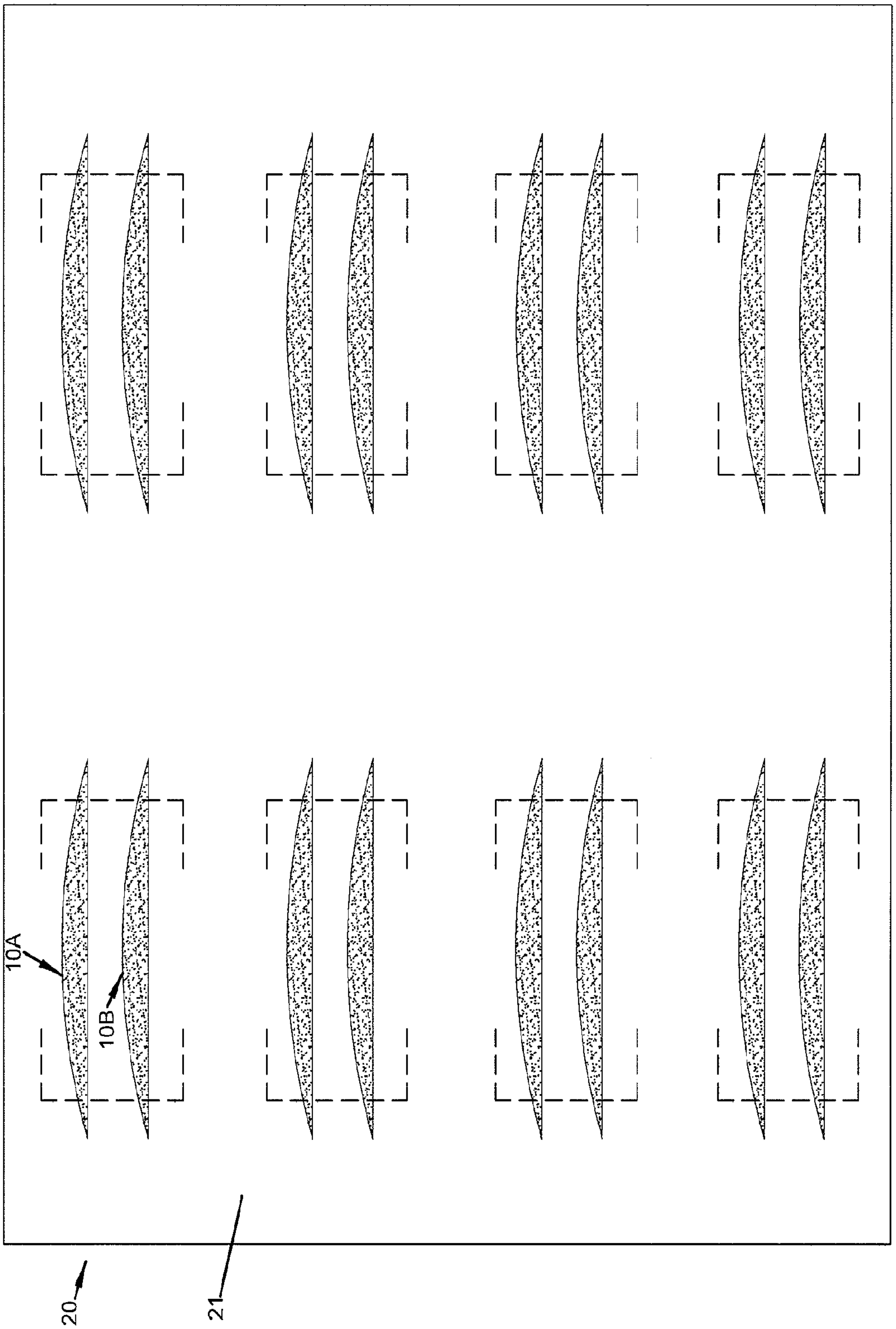
FIG. 3*a* is a diagram showing another embodiment of the invention including eight pairs of eye strips 10A and 10B positioned on the backing material card 20.
Figure 3B:
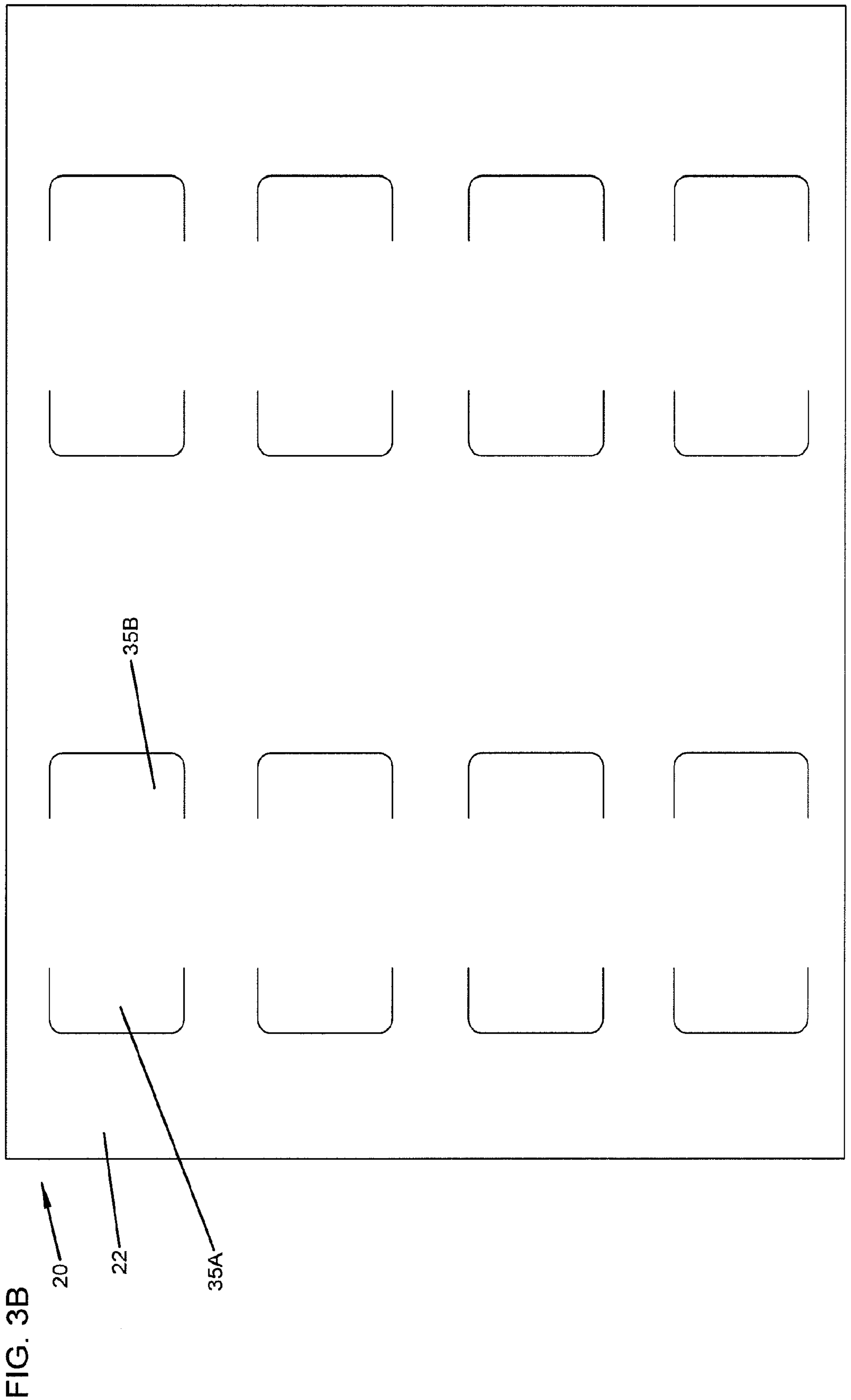
FIG. 3*b* is a diagram showing the back surface 22 of the embodiment shown in FIG. 3*a*.

In one embodiment each backing card holds 8 pairs of strips, as shown in FIGS. 3*a* and 4*a*. Each card can be placed in a re-sealable wrapper. Since there are multiple pairs of strips per card, the user can re-insert the card into the wrapper after removing a single pair of strips.

Because the skin of the upper eyelid is fragile, eye strip removal must be accomplished without placing undue shearing or pulling stress on the skin which could result in skin tearing. As a result, it is recommended that moisturizer be applied to the skin of the upper eyelid prior to placement of the strip. Since moisturizer is present, the adhesive must be of a more aggressive nature to overcome the slipperiness of the moisturizer. This is preferable to using a less aggressive adhesive without moisturizer, which may cause greater difficulty with strip removal when adhesive contacts the skin directly without any intervening moisturizer.

It is necessary for the unused strips to adhere well enough to the backing card so as to not slide into and adhere to an adjacent strip or become positioned away from the vertical cut or over the horizontal cut extensions rendering the removal mechanism less effective or ineffective. It is also necessary that the level of adhesion not be so great as to increase the force required to lift the ends of the strip off the backing material. As noted above, the adhesive on the strip must be relatively aggressive so it can be placed over and used with a moisturizer. Therefore, to reduce the adhesion between strip and backing material to an extent that the lifting force is not excessive, but yet not to reduce the adhesion to a degree where strips slide out of position, a number of suitable chemical substances, such as a release coating, can be applied to the backing material, positioned between the paper of the backing material card and the adhesive coating of the strip. These substances include silicone and similar materials.

Although in this embodiment a pair of strips are shown in reference to the release mechanism, the release mechanism could be used with a single strip or more than two. Other configurations of the continuous cuts, such as wavy, zig-zag or curved lines, are contemplated, as long as the cut or cuts result in forming a movable flap in the backing material positioned proximal to the end region of an adhesive eye strip. Indicia indicating where the user should press upwards on the backing material under an adhesive eye strip to facilitate strip removal are also contemplated. The adhesive eye strips can be packaged in convenient quantities, for example, a one-week or a one-month supply, for daily use by the user.

What is claimed is:

1. An adhesive eye strip release mechanism, comprising:
- an adhesive eye strip comprising a flexible material coated with an adhesive layer; and
- a backing material card onto which the eye strip is positioned, the card having at least one continuous vertical cut and at least one continuous horizontal cut, said vertical and horizontal cuts having at least one point of intersection, wherein at least a portion of the continuous vertical cut or the continuous horizontal cut is covered by the adhesive layer of the eye strip, and wherein said vertical and horizontal cuts are capable of creating a movable flap from which the eye strip can be removed.

2. The release mechanism of claim 1, wherein the at least one vertical cut intersects with at least two horizontal cuts to create the movable flap.

3. The release mechanism of claim 1, wherein the backing material card includes a release coating.

4. The release mechanism of claim 1, wherein the movable flap is configured to lift one end of the eye strip off of the backing material card.

5. The release mechanism of claim 1, comprising a plurality of movable flaps positioned under the eye strip.

6. The release mechanism of claim 5, wherein the movable flaps are configured to lift either end of the eye strip off of the backing material card.

7. The release mechanism of claim 1, wherein the continuous cut is generally linear.

8. A method for applying an adhesive eye strip to an eyelid, comprising the steps of:
- a) providing an eye strip on a backing material card, said card comprising a movable flap;
- b) lifting the movable flap upwards to release one end of the eye strip from the backing material card;
- c) lifting the released end of the eye strip to remove the entire eye strip from the movable flap; and
- d) applying the eye strip to the eyelid after removing the entire eye strip from the movable flap.

9. The release mechanism of claim 1, wherein said vertical and horizontal cuts are located within a perimeter of the backing material card.

10. An adhesive eye strip release mechanism, comprising:
- an adhesive eye strip comprising a flexible material coated with an adhesive layer; and
- a backing material card onto which the eye strip is positioned, the card having at least one continuous curved cut to create a movable flap from which the eye strip can be removed by lifting the movable flap upwards to release one end of the eye strip from the backing material card, wherein at least a portion of the continuous curved cut is covered by the adhesive layer of the eye strip.

11. The release mechanism of claim 10, wherein the backing material card includes a release coating.

12. The release mechanism of claim 10, wherein the movable flap is configured to lift one end of the eye strip off of the backing material card.

13. The release mechanism of claim 10, comprising a plurality of movable flaps positioned under the eye strip.

14. The release mechanism of claim 13, wherein the movable flaps are configured to lift either end of the eye strip off of the backing material card.

15. The release mechanism of claim 10, wherein said continuous curved cut is located within a perimeter of the backing material card.

* * * * *